United States Patent [19]

Diederen et al.

[11] 4,353,909
[45] Oct. 12, 1982

[54] 6-HYDROXY-2-PHENYL-IMIDAZO[4,5-B]PYRIDINES AND SALTS THEREOF

[75] Inventors: Willi Diederen; Axel Prox; Albert Reuter; Willy Roth, all of Biberach; Jochen Schmid, Warthausen, all of Fed. Rep. of Germany

[73] Assignee: Dr. Karl Thomae Gesellschaft mit beschränkter Haftung, Biberach, Fed. Rep. of Germany

[21] Appl. No.: 305,159

[22] Filed: Sep. 24, 1981

[30] Foreign Application Priority Data

Oct. 3, 1980 [DE] Fed. Rep. of Germany ....... 3037464

[51] Int. Cl.$^3$ .................... A61K 31/44; C07D 487/04
[52] U.S. Cl. .................................. 424/256; 546/118
[58] Field of Search .................... 546/118; 424/256

[56] References Cited

U.S. PATENT DOCUMENTS 3,985,891  12/1976  Kutter et al. .................... 546/118

Primary Examiner—Norma S. Milestone
Attorney, Agent, or Firm—Hammond & Littell, Weissenberger & Muserlian

[57] ABSTRACT

Compounds of the formula

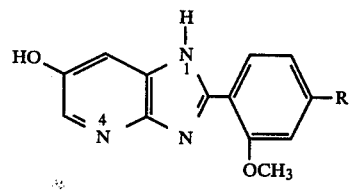

wherein R is methylsulfinyl or methylsulfonyl, their 3H-tautomers, and non-toxic, pharmacologically acceptable acid addition salts thereof. The compounds are useful as cardiotonics.

5 Claims, No Drawings

6-HYDROXY-2-PHENYL-IMIDAZO[4,5-B]PYRIDINES AND SALTS THEREOF

This invention relates to novel derivatives of 6-hydroxy-2-(2-methoxy-phenyl)-imidazo[4,5-b]pyridine and non-toxic acid addition salts thereof, to a method of preparing these compounds, to pharmaceutical compositions containing them as active ingredients, and to a method of using them as cardiotonics.

More particularly, the present invention relates to a novel class of compounds represented by the formula

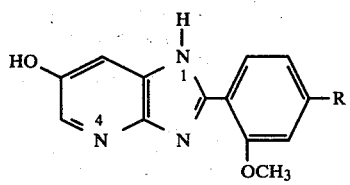

wherein R is methylsulfinyl or methylsulfonyl, their 3H-tautomers, and non-toxic, pharmacologically acceptable acid addition salts thereof.

The compounds embraced by formula I and their 3H-tautomers may be prepared by nucleus hydroxylation of a compound of the formula

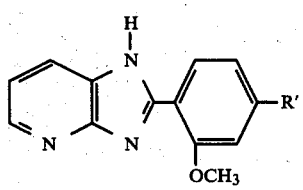

wherein R' is methylmercapto, methylsulfinyl or methylsulfonyl.

The nucleus hydroxylation is preferably performed in a solvent such as water, tert. butanol or a polyethyleneglycol ether like dimethoxy diethylene glycol or mixtures thereof; in the presence of an oxidizing agent, for instance a peroxide compound such as hydrogen peroxide, peroxydisulfonic acid or peroxysulfuric acid, or chromic acid or a $Ce^{IV}$—, $V^{V}$— or $Mn^{VII}$-compound such as ceric nitrate, potassium permanganate or vanadium pentoxide; advantageously in the presence of a reaction accelerator such as a salt of iron, copper, manganese or vanadium, for instance copper sulfate, iron-II-chloride, manganese-II-acetate or vanadyl sulfate; preferably in the pH-range of 4.0–8.5; and at a temperature between 0° and 100° C., preferably between 20° and 35° C. The activity of the metal ions may be controlled with the aid of a complex-former such as ethylenediamine tetraacetic acid, nitrilotriacetic acid or ascorbic acid, or with a crown ether such as 18-crown-6. Especially advantageous is the hydroxylation reaction in the presence of a buffer, such as a phosphate buffer, and with a 1.1- to 3.5-fold excess of the peroxy-compound.

The reaction may also be carried out enzymatically, for instance by using hydroxylases, monoxygenases or peroxidases.

The compounds of the formula I and their 3H-tautomers are basic and therefore form addition salts with inorganic or organic acids. Examples of non-toxic, pharmacologically acceptable acid addition salts are those formed with hydrochloric acid, hydrobromic acid, sulfuric acid, lactic acid, citric acid, tartaric acid, maleic acid or fumaric acid.

The starting compounds needed for the above-described method of preparation of the compounds of the present invention are described in the literature. For example, they may be obtained by subjecting 2,3-diaminopyridine to a ring closure reaction with a corresponding benzoic acid derivative, optionally followed by oxidation.

The following example illustrates the present invention and will enable others skilled in the art to understand it more completely. It should be understood, however, that the invention is not limited solely to the particular example given below.

EXAMPLE 1

2-(2-Methoxy-4-methylsulfinyl-phenyl)-6-hydroxy-1H-imidazo[4,5-b]pyridine and 2-(2-Methoxy-4-methylsulfonyl-phenyl)-6-hydroxy-1H-imidazo[4,5-b]pyridine 7.2 gm of 2-(2-methoxy-4-methylsulfinyl-phenyl)-1H-imidazo[4,5-b]pyridine were dissolved in a mixture of a phosphate buffer of pH 7.2 and 120 ml of 3% hydrogen peroxide, and a solution of 9.3 gm of ethylenediamine tetraacetic acid, 4.4 gm of ascorbic acid, 3.8 gm of iron-(II) sulfate in a phosphate buffer of pH 7.2 was added. After 30 minutes the reaction mixture was evaporated in vacuo, and the residue was purified by chromatography on a polystyrene resin column (XAD-2 of Röhm & Haas) with water and methanol as eluants. After evaporation of the eluate the two compounds were separated by means of chromatography on silicagel [eluant: chloroform/methanol/ammonia water=85/15/2 (v/v)].

2-(2-Methoxy-4-methylsulfinyl-phenyl)-6-hydroxy-1H-imidazo[4,5-b]pyridine was obtained as yellow powder.

M.p.: 220°–223° C.

Calc.: C-55.45%; H-4.29%; N-13.86%; S-10.56%.
Found: C-54.10%; H-4.49%; N-13.74%; S-11.15%.

2-(2-Methoxy-4-methylsulfonyl-phenyl)-6-hydroxy-1H-imidazo[4,5-b]pyridine was obtained as yellow powder.

M.p.: 250° C. (decomp.).

Calc.: C-52.66%; H-4.08%; N-13.17%; S-10.03%.
Found: C-52.15%; H-4.34%; N-13.27%; S-11.45%.

The compounds of the present invention, that is, those embraced by formula I above, their 3H-tautomers, and non-toxic, pharmacologically acceptable acid addition salts thereof, have useful pharmacodynamic properties. More particularly, they exhibit very effective positive inotropic activity with minor concurrent effect on blood pressure and heart rate in warm-blooded animals, such as cats.

The above pharmacological properties of the compounds of the present invention were ascertained by the following method, where A=2-(2-Methoxy-4-methylsulfinyl-phenyl)-6-hydroxy-1H-imidazo[4,5-b]pyridine, and B=2-(2-Methoxy-4-methylsulfonyl-phenyl)-6-hydroxy-1H-imidazo[4,5-b]pyridine.

2–3 Cats of both sexes having a body weight of 3.2 to 3.6 kg were anesthetized with 40 mg/kg i.p. of pentobarbital sodium. The trachea was opened, and the animals breathed spontaneously through a tracheal cannula during the test. The positive inotropic effect was determined by measuring the pressure in the left auricle by means of a catheter tip manometer (Millar PC 350 A). The contractility parameters $dp/dt_{max}$ and $V_{CE}$ were registered by means of an analog differentiating circuit. The arterial blood pressure was measured in the aorta abdominalis by a Statham pressure transducer (P 23 Dc). The heart rate was determined by means of a tachograph controlled by the E.C.G. All parameters were directly recorded by means of a Hellige direct writer.

The test substances were dissolved in a mixture of polydiol 200 and 0.9% sodium chloride solution. The substances were used in a 0.1% solution (dose: 0.1 or 0.3 mg/kg i.v.) and in a 1% solution (dose: 1.0 or 3.0 mg/kg i.v.). All substances were cumulatively dosed at intervals of 10 minutes. The following table shows the results which were obtained and the total doses.

| Compound | Dose mg/kg i.v. | Change in blood pressure mm/Hg | Change in % | | |
|---|---|---|---|---|---|
| | | | $dp/dt_{max}$ | $VC_E$ | heart rate |
| A | 0.1 | 0 | +10.8 | +12.1 | +1.5 |
| | 0.3 | 0 | +22.4 | +19.8 | +1.5 |
| | 1.0 | 0 | +32.4 | +28.9 | +1.5 |
| | 3.0 | 0 | +66.6 | +48.6 | +4.7 |
| B | 0.1 | +3/5 | +13.9 | +13.4 | +0 |
| | 0.3 | +8/8 | +41.5 | +34.6 | +5.6 |
| | 1.0 | +10/8 | +79.8 | +60.6 | +9.7 |
| | 3.0 | +13/5 | +116.8 | +96.1 | +10.4 |

Supplemental to the above, it should be pointed out that neither compound exhibited any toxic side-effects, even when administered at the highest dose. Moreover, the new compounds show significantly more polar structure than the starting materials. Therefore, they can be easily eliminated, without an additional biotransformation, i.e. the organism is only slightly burdened by these compounds, particularly since epoxide formation is hindered by the hydroxy substituent.

Based on their pharmacological properties, the compounds of the present invention, their 3H-tautomers and non-toxic, pharmacologically acceptable acid addition salts thereof are useful for the tratment of myocardia.

For pharmaceutical purposes the compounds of the present invention are administered to warm-blooded animals perorally, parenterally or rectally as active ingredients in customary dosage unit compositions, that is, compositions in dosage unit form consisting essentially of an inert pharmaceutical carrier and one effective dosage unit of the active ingredient, such as tablets, coated pills, capsules, wafers, powders, solutions, suspensions, emulsions, syrups, suppositories and the like. One effective dosage unit of the compounds according to the present invention is from 0.5 to 3.57 mgm/kg body weight, preferably 0.7 to 1.43 mgm/kg body weight, 2 to 4 times daily.

The following examples illustrate a few pharmaceutical dosage unit compositions comprising a compound of the present invention as an active ingredient and represent the best modes contemplated of using the invention. The parts are parts by weight unless otherwise specified.

EXAMPLE 2

Tablets

The tablet composition is compounded from the following ingredients:

| | |
|---|---|
| 2-(2-Methoxy-4-methylsulfinyl-phenol)-6-hydroxy-1H-imidazo[4,5-b]pyridine | 100.0 parts |
| Lactose | 50.0 parts |
| Polyvinyl pyrrolidone | 5.0 parts |
| Carboxymethyl cellulose | 19.0 parts |
| Magnesium stearate | 1.0 parts |
| Total | 175.0 parts |

Preparation:
Moist screening: 1.5 mm
Drying: in a circulation air drier at 50° C.
Dry screening: 1 mm The granulate and the remaining auxiliary products are admixed and compressed into tablets.
Weight of each tablet: 175 mg
Punch: 8 mmφ.

EXAMPLE 3

Coated Pills

The pill core composition is compounded from the following ingredients:

| | |
|---|---|
| 2-(2-Methoxy-4-methylsulfinyl-phenyl)-6-hydroxy-1H-imidazo-[4,5-b]pyridine | 50.0 parts |
| Corn starch, dried | 20.0 parts |
| Soluble starch | 2.0 parts |
| Carboxymethyl cellulose | 7.0 parts |
| Magnesium stearate | 1.0 parts |
| Total | 80.0 parts |

Preparation:
The active ingredient and the corn starch are homogeneously moistened with an aqueous solution of the soluble starch.
Moist screening: 1.0 mm
Dry screening: 1.0 mm
Drying: in a circulation air drier at 50° C.

The granulate and the remaining auxiliary products were admixed and compressed into pill cores.
Weight of each core: 80 mg
Punch: 6 mm
Radius of curvature: 5 mm The finished cores are covered with a sugar coating in conventional manner.
Weight of each coated pill: 120 mg.

EXAMPLE 4

Suppositories

The suppository composition is compounded from the following ingredients:

| | |
|---|---|
| 2-(2-Methoxy-4-methylsulfinyl-phenyl)-6-hydroxy-1H-imidazo-[4,5-b]pyridine | 75.0 parts |
| Suppository base (e.g. cocoa butter) | 1625.0 parts |
| Total | 1700.0 parts |

Preparation:
The suppository base is melted. At 38° C. the pulverized active ingredient is homogeneously dispersed in the melt. The composition is cooled to 35° C. and poured into pre-cooled suppository molds.
Weight of each suppository: 1.7 gm

EXAMPLE 5

Hypodermic Solution

The solution is compounded from the following ingredients:

| | |
|---|---|
| 2-(2-Methoxy-4-methylsulfinyl-phenyl)-6-hydroxy-1H-imidazo-[4,5-b]pyridine | 50.0 parts |
| Sorbitol | 250.0 parts |
| Distilled water q.s. ad | 5000.0 parts by vol. |

Preparation:

The active ingredient and the sorbitol are dissolved in sufficient distilled water, and the solution is diluted with distilled water to the given volume and steril-filtered.

Bottling: into ampules containing 5 ml
Sterilization: 20 minutes at 120° C.

EXAMPLE 6

Drop Solution

The solution is compounded from the following ingredients:

| | |
|---|---|
| 2-(2-Methoxy-4-methylsulfinyl)-phenyl)-6-hydroxy-1H-imidazo-[4,5-b]pyridine | 5.0 parts |
| Methyl p-hydroxybenzoate | 0.035 parts |
| Propyl p-hydroxybenzoate | 0.015 parts |
| Oil of anise | 0.05 parts |
| Menthol | 0.06 parts |
| Saccharin sodium | 1.0 parts |
| Glycerin | 10.0 parts |
| Ethanol | 40.0 parts |
| Water, distilled q.s. ad | 100.0 parts by vol. |

Preparation:

The hydroxybenzoates are dissolved in the ethanol, and the oil of anise and the menthol are added. Subsequently, a solution of the glycerin and the saccharin sodium in the distilled water is added, and the solution is filtered until clear. 5 ml of the solution contain 250 mgm of the active ingredient.

Any one of the other compounds embraced by formula I, the 3H-tautomer thereof, or a non-toxic, pharmacologically acceptable acid addition salt thereof may be substituted for the particular active ingredient in Examples 2 through 6. Likewise, the amount of the active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A compound of the formula

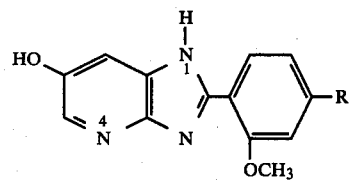

wherein R is methylsulfinyl or methylsulfonyl, its 3H-tautomer, or a non-toxic, pharmacologically acceptable acid addition salt thereof.

2. A compound of claim 1, which is 2-(2-methoxy-4-methylsulfinyl-phenyl)-6-hydroxy-1H-imidazo[4,5-b]pyridine, or a non-toxic, pharmacologically acceptable acid addition salt thereof.

3. A compound of claim 1, which is 2-(2-methoxy-4-methylsulfonyl-phenyl)-6-hydroxy-1H-imidazo[4,5-b]pyridine, or a non-toxic, pharmacologically acceptable acid addition salt thereof.

4. A cardiotonic pharmaceutical dosage unit composition consisting essentially of an inert pharmaceutical carrier and an effective cardiotonic amount of a compound of claim 1.

5. The method of increasing the strength of the heart muscle contraction in a warm-blooded animal in need thereof, which comprises perorally, parenterally or rectally administering to said animal an effective positive inotropic amount of a compound of claim 1.

* * * * *

UNITED STATES PATENT AND TRADEMARK OFFICE
CERTIFICATE OF CORRECTION

PATENT NO. : 4,353,909

DATED : October 12, 1982

INVENTOR(S) : Willi Diederen et al.

It is certified that error appears in the above—identified patent and that said Letters Patent is hereby corrected as shown below:

Column 1, line 40: "polye-" should be -- poly- --.

Column 1, line 41: "thyleneglycol" should be -- ethyleneglycol --

Column 4, line 2: "phenol)-6-" should be -- phenyl)-6- --.

Signed and Sealed this

Twenty-eighth Day of December 1982

[SEAL]

Attest:

GERALD J. MOSSINGHOFF

Attesting Officer    Commissioner of Patents and Trademarks